US006958351B2

(12) United States Patent
Chenard et al.

(10) Patent No.: US 6,958,351 B2
(45) Date of Patent: Oct. 25, 2005

(54) NMDA NR2B ANTAGONISTS FOR TREATMENT

(75) Inventors: Bertrand L. Chenard, Waterford, CT (US); Mario Saltarelli, Lake Bluff, IL (US); Frank S. Menniti, Mystic, CT (US)

(73) Assignee: Pfizer Inc, New York, NY (US)

(*) Notice: Subject to any disclaimer, the term of this patent is extended or adjusted under 35 U.S.C. 154(b) by 677 days.

(21) Appl. No.: 09/969,318

(22) Filed: Oct. 2, 2001

(65) Prior Publication Data

US 2004/0162312 A1 Aug. 19, 2004

Related U.S. Application Data

(60) Provisional application No. 60/237,770, filed on Oct. 2, 2000.

(51) Int. Cl.$^7$ ............................................. A61K 31/445
(52) U.S. Cl. ...................... 514/327; 514/315; 514/323
(58) Field of Search ................................. 514/315, 323, 514/327, 304, 278, 216

(56) References Cited

U.S. PATENT DOCUMENTS 5,710,168 A * 1/1998 Chenard ...................... 514/327
6,046,213 A * 4/2000 Chenard et al. ............. 514/327

FOREIGN PATENT DOCUMENTS

| EP | 0768086 | 4/1997 |
|---|---|---|
| EP | 0787493 | 8/1997 |
| WO | WO9707098 | 2/1997 |
| WO | WO 97/07098 A1 * | 2/1997 |
| WO | WO97/23202 | 7/1997 |
| WO | WO9723214 | 7/1997 |
| WO | WO9723215 | 7/1997 |
| WO | WO9723216 | 7/1997 |
| WO | WO9723458 | 7/1997 |
| WO | WO9944610 | 9/1999 |
| WO | WO9944640 | 9/1999 |
| WO | WO0000197 | 1/2000 |

OTHER PUBLICATIONS

Stedman's Medical Dictionary, 25$^{TH}$ Edition, Illustrated, pp. 1286 and 1287, 1994.*

Hironaka, N., et al., Neuroscience Letters, vol. 288, No. 2, 2000, pp. 139–142, XP001077717.

Butler, T.W., et al., J. Med. Chem., vol. 41, 1998, pp. 1172–1184, XP001073767.

Menniti, Frank, et al., CP–101, 606, a potent neuroprotectant selective for forebrain neurons, European Journal of Pharmacology 331 (1997) pp. 117–126, XP–001150396.

Parsons, Chris G., et al., Glutamate in CNS Disorders as a Target for Drug Development: An Update, Drug News Perspect 11(9), Nov. 1998, pp. 523–569, XP–000910825.

Tamiz, Amir P., et al., Structure–Activity Relationships for a Series of Bis(phenylalkyl)amines: Potent Subtype—Selective Inhibitors of N–Methyl–D–aspartate Receptors, J. Med. Chem. 1998, 41, pp. 3499–3506, XP–001151638.

Taniguchi, Kana, et al., Antinoclceptive activity of CP–101, 606, an NMDA receptor NR2B subunit antagonist, British Journal of Pharmacology (1997) 122, pp. 809–812.

Boyce S., et al., Selective NMDA NR2B antagonists induce antinociception without motor dysfunction: correlation with restricted localisation of NR2B subunit in dorsal horn, Neuropharmacology 38, (1999) pp. 611–623, XP–001077718.

Albin, Roger L. and Sid Gilman, Autoradiographic localization of inhibitory and excitatory amino acid neurotransmitter receptors in human normal and olivopontocerebellar atrophy cerebellar cortex, Brain Research, 522 (1990) pp. 37–45, XP008016404.

Lagré ze, Wolf A., N–methyl–D–aspartate receptor subunit mRNA expression in human retinal ganglion cells, Graefs Arch Clin Exp Ophthalmol (2000) 238: pp. 486–490, XP–001151637.

Dreyer, Evan B., et al., Greater sensitivity of larger retinal ganglion cells to NMDA–mediated cell death, NeuroReport 5, pp. 629–631 (1994), XP008016376.

Kapin, Michael A., et al., Neuroprotective Effects of Eliprodil in Retinal Excitoxity and Ischemia, IOVS, May 1999, vol. 40, No. 6, pp 1177–1182, XP008016405.

Chenard, B.L., et al., (1S,2S)–1–(4–Hydroxyphenyl)–2–(4–hydroxy–4–phenyl piperidino)–1–propanol: A Potent New Neuroproctectant Which Blocks N–Methyl–D–aspartate Responses, J. Med. Chem. 1995, 38, pp. 3138–3145, XP–000999280.

Menniti, Frank S., CP–101,606, an NR2B subunit selective NMDA receptor antagonist, inhibits NMDA and injury induced c–fos expression and cortical spreading depression in rodents, Neuropharmacology 39 (2000) pp. 1147–1155, XP–001074732.

Menniti Frank S., et al., CP–101,606: An NR2B–selective NMDA receptor antagonist, CNS Drug Reviews, vol. 4, No. 4, Jan. 1, 1998, pp. 307–322, XP008003933.

* cited by examiner

*Primary Examiner*—Dwayne Jones
(74) *Attorney, Agent, or Firm*—Peter C. Richardson; Lorraine B. Ling; Andrea E. Dorigo

(57) ABSTRACT

The invention provides new methods for treating certain disorders resulting from neurodegeneration and for treating depression which comprise administration of NR2B subunit selective NMDA antagonists. The disorders that can be treating by the invention include hearing loss, vision loss, neurodegeneration caused by epileptic seizures, neurotoxin poisoning, Restless Leg Syndrome, multi-system atrophy, non-vascular headache, and depression.

2 Claims, No Drawings

NMDA NR2B ANTAGONISTS FOR TREATMENT

This application claims priority under 35 U.S.C. 119(e) of U.S. Provisional Application No. 60/237,770, filed Oct. 2, 2000.

FIELD OF THE INVENTION

This invention relates to the treatment of neurological disorders. This invention also relates to the treatment of depression. More particularly, this invention relates to treatment of hearing loss, vision loss, neurodegeneration caused by epileptic seizures, neurotoxin poisoning, Restless Leg Syndrome, multi-system atrophy, non-vascular headache, and depression comprising administering an N-methyl-D-aspartate (NMDA) NR2B subtype receptor antagonist.

BACKGROUND OF THE INVENTION

NMDA Receptors and NMDA Receptor Subunits

Glutamate and aspartate play dual roles in the central nervous system as essential amino acids and as the principal excitatory neurotransmitters (hereinafter referred to as excitatory amino acids or EAAs). There are at least four classes of EAA receptors: NMDA, AMPA (2-amino-3-(methyl-3-hydroxyisoxazol-4-yl)propanoic acid), kainate and metabotropic receptors. These EAA receptors mediate a wide range of signaling events that impact all physiological brain functions. For example, it has been reported that NMDA receptor antagonists produce an analgesic effect under certain conditions (Wong, C. S., Cherng, C. H. and Ho, S. T., *Clinical Applications of Excitatory Amino Acid Antagonists in Pain Management Acta Anaesthesiologica. Sinica;* 33, 227–232 (1995)).

The NMDA receptor is an ion channel permeable to $Na^+$ and $Ca^{2+}$. The receptor is gated by synaptically released glutamate in the presence of co-agonist glycine and concomitant depolarization (Mayer, M. L. and Westbrook, G. L., *The Physiology of Excitatory Amino Acids in the Vertebrate Nervous System, Progress in Neurobiology,* 28, 197–276 (1987)). Thus, NMDA receptor activity may be attenuated by blockade, for example, of 1) the glutamate binding site, 2) the glycine co-agonist binding site, or 3) the site of the ion channel.

The NMDA receptor is composed of multiple protein subunits (Seeburg, P. H., *The Molecular Biology of Mammalian Glutamate Receptor Channels, Trends in Neurosci.,* 16, 359–365 (1993)). The protein subunits fall into two categories: NR2 and NR1. The NR2 subunits contain glutamate binding sites, whereas the NR1 subunits contain the glycine binding sites. Five subunits have been cloned to date, namely NR1 and NR2A, NR2B, NR2C and NR2D. Expression studies indicate the functional receptor is composed of at least one NR1 site and one or more of the NR2 sites. Thus, different subtypes of NMDA receptors can be categorized based on their particular NR2 subunit composition. For example, in the adult mammalian brain, the NR1 and NR2A subunits are widely expressed, forming a subtype of NMDA receptor comprising an NR2A subunit. In contrast, NR2B subunit expression is mostly localized in forebrain regions including cortex, hippocampus and striatum; the NR2C subunit is expressed in the cerebellum; and the NR2D subunit is restricted to the midbrain region. NMDA receptor subtypes of corresponding composition can accordingly respectively be found in forebrain, cerebellum, and midbrain.

Compounds that inhibit NMDA receptor activity by interacting at the glutamate, glycine, or receptor-associated ion channel as described above have little (<10-fold) selectivity across the different NMDA receptor subtypes. That is, such compounds inhibit NMDA receptors with potencies within a 10-fold range regardless of the subunit combination. However, the subunit composition of the NMDA receptor can confer unique physiology with regard to conductance, kinetics, and affinity for certain agonists. For example, the subunit composition of an NMDA receptor has significant effects on its sensitivity to a group of allosteric modulators which include protons, polyamines, $Zn^{2+}$, and oxidizing/reducing agents (Chenard, B. L. and Menniti, F. S., *Antagonists Selective for NMDA Receptors Containing the NR2B Subunit, Current Pharmaceutical Design,* 1999, 5:381–404)). Receptors comprising the NR2B subunit possess a unique site to which compounds may bind, resulting in specific inhibition this subtype of NMDA receptor as compared to NMDA receptors that do not comprise an NR2B subunit (Ibid). This unique site is distinct from the glutamate binding site on the NR2B subunit.

Antagonizing NMDA receptors at the NR2B subunit specific binding site can be used to substantially avoid side effects that have been noted at therapeutic drug levels with other non-specific NMDA receptor antagonists. Both glutamate competitive antagonists and channel blocking agents cause cardiovascular effects and psychotic symptoms in man (Chenard and Menniti, supra). In rodents, these types of compounds also cause locomotor hyperactivity and a paradoxical neuronal hyperexcitability manifest as neuronal vacuolization in cingulate and retrosplenial cortices (Id.). Antagonists at the glycine co-agonist site cause less locomoter activation and do not cause neuronal vacuolization at neuroprotective doses in rodents, however physicochemical problems (for example, problems relating to solubility, brain penetration and protein binding) associated with the quinoxalinedione nucleus typical of such compounds have hindered efforts to bring this class of molecules forward in the clinic (Id). NMDA receptor antagonists selective for the NR2B subunit offer a means of inhibition without the side effects and psychochemical difficulties described above.

NR2B Subunit Selective NMDA Receptor Antagonists

Compounds that inhibit NMDA receptors comprising an NR2B subunit by specific binding to the NR2B subunit have been demonstrated by measurement of inhibition of NMDA-induced current in *Xenopus* Oocytes cotransfected with the genes expressing the NR1 and NR2B subunits (Chenard and Menniti, supra). Specificity for NR2B can be confirmed by observing reduced inhibition of the NMDA-induced current in *Xenopus* Oocytes cotransfected with an NR1 subunit and an NR2 subunit other than NR2B.

A number of compounds have been found to act as antagonists that target the NR2B subunits of NMDA receptors that contain them. The first compound identified to display significant affinity for the NR2B subunit was ifenprodil. Ifenprodil is both more potent and efficacious for blockade of ion current through NMDA receptors comprised of NR1/NR2B subunits compared to NR1/NR2A, NR2C, or NR2D subunits.

For example, ifenprodil and related compounds have been demonstrated in animal models of pain perception to produce significant analgesic activity (Bernardi, M., Bertolini, A., Szczawinska, K. And Genedani, S., *Blockade of the Polyamine Site of NMDA Receptors Produces Antinociception and Enhances the Effect of Morphine, in Mice,* European Journal of Pharmacology, 298, 51–55, (1996); Taniguchi, K., Shinjo, K., Mizutani, M., Shimada, K., Ishikawa, T., Menniti, F. S. and Nagahisa, A, *Antinociceptive Activity of CP*-101,606, *an NMDA Receptor NR2B Subunit Antagonist,* British Journal of Pharmacology, 122, 809–812 (1997)).

U.S. Pat. No. 5,710,168 (issued Jan. 20, 1998) claims the use of certain compounds of formula I, infra, having NR2B subunit selectivity for treating a disease or condition which is susceptible to treatment by blocking of NMDA receptor sites, including traumatic brain injury, spinal cord trauma, pain, psychotic conditions, drug addiction, migraine, hypoglycemia, anxiolytic conditions, urinary incontinence, and ischemic events arising from CNS surgery, open heart surgery or any procedure during which the function of the cardiovascular system is compromised.

U.S. Ser. No. 09/397,891, filed Sep. 17, 1999, pertains to a method of treating acute, chronic and/or neuropathic pain comprising administering an NR2B selective NMDA receptor antagonist, for example a compound of formula I, infra.

U.S. Pat. No. 5,710,168 and U.S. Ser. No. 09/397,891 are both incorporated by reference herein in their entireties.

SUMMARY OF THE INVENTION

The present invention provides a method for treating sensorineural hearing loss in a mammal, which method comprises administering to the mammal an amount of an NR2B subunit selective NMDA antagonist, which amount is effective in treating sensorineural hearing loss.

This invention also provides a method for treating neurological damage caused by epileptic seizures in a mammal, which method comprises administering to the mammal an amount of an NR2B subunit selective NMDA antagonist, which amount is effective in inhibiting neurological damage.

This invention further provides a method for treating neurological damage caused by neurotoxin poisoning in a mammal, which method comprises administering to the mammal an amount of an NR2B subunit selective NMDA antagonist, which amount is effective in inhibiting neurological damage.

This invention further provides a method for treating vision loss caused by neurodegeneration of the visual pathway in a mammal, which method comprises administering to the mammal an amount of an NR2B subunit selective NMDA antagonist, which amount is effective in treating vision loss caused by neurodegeneration of the visual pathway.

This invention also provides a method of treating Restless Leg Syndrome in a mammal, which method comprises administering to the mammal an amount of an NR2B subunit selective NMDA antagonist, which amount is effective in treating Restless Leg Syndrome.

This invention also provides a method of treating multi-system atrophy in a mammal, which method comprises administering to the mammal an amount of an NR2B subunit selective NMDA antagonist, which amount is effective in treating multi-system atrophy.

This invention also provides a method of treating non-vascular headache in a mammal, which method comprises administering to the mammal an amount of an NR2B subunit selective NMDA antagonist, which amount is effective in treating non-vascular headache.

This invention also provides a method of treating depression in a mammal, which method comprises administering to the mammal an amount of an NR2B subunit selective NMDA antagonist, which amount is effective in treating depression.

In one embodiment, the NR2B subunit selective NMDA antagonist in each of the preceding methods is a compound of formula I

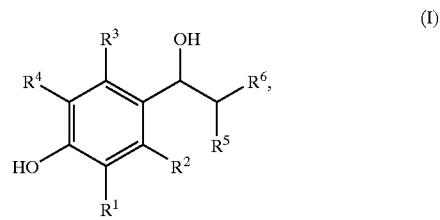

(I)

or a pharmaceutically acceptable acid addition salt thereof or an enantiomer thereof, wherein:

(a) $R^2$ and $R^5$ are taken separately and $R^1$, $R^2$, $R^3$ and $R^4$ are each independently hydrogen, $(C_1-C_6)$ alkyl, halo, $CF_3$, OH or $OR^7$ and $R^5$ is methyl or ethyl; or (b) $R^2$ and $R^5$ are, taken together,

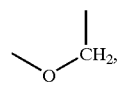

thereby forming a chroman-4-ol ring, and $R^1$, $R^3$ and $R^4$ are each independently hydrogen, $(C_1-C_6)$ alkyl, halo, $CF_3$, OH or $OR^7$;

$R^6$ is

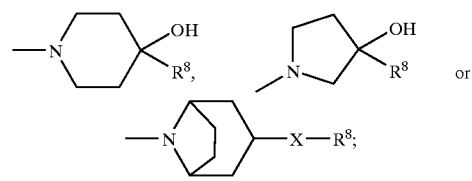

$R^7$ is methyl, ethyl, isopropyl or n-propyl;

$R^8$ is phenyl optionally substituted with up to three substituents independently selected from the group consisting of $(C_1-C_6)$ alkyl, halo and $CF_3$;

X is O, S or $(CH_2)_n$; and n is 0, 1, 2, or 3.

In another embodiment of each of the preceding methods, the NR2B subunit selective NMDA antagonist is:

(+)-(1S,2S)-1-(4-hydroxy-phenyl)-2-(4-hydroxy-4-phenylpiperidino)-1-propanol;

(1S,2S)-1-(4-hydroxy-3-methoxyphenyl)-2-(4-hydroxy-4-phenylpiperidino)-1-propanol;

(3R,4S)-3-(4-(4-fluorophenyl)-4-hydroxypiperidin-1-yl)-chroman-4,7-diol; or (1R*,2R*)-1-(4-hydroxy-3-methylphenyl)-2-(4-(4-fluorophenyl)-4-hydroxypiperidin-1-yl)-propan-1-ol; or an enantiomer of one of the aforementioned compounds; or a pharmaceutically acceptable acid addition salt of one of the aforementioned compounds or one of their enantiomers.

DETAILED DESCRIPTION OF THE INVENTION

"Mammal" as used herein refers to any mammal, including humans.

The phrase "sensorineural hearing loss" refers to hearing loss caused by loss of neurons. Such hearing loss can be, for example, genetic in origin. Another example of sensorineural hearing loss is antibiotic-induced, such as aminoglycoside-induced, hearing loss. Sensorineural hearing loss can also be induced by excessive sound.

"Neurotoxin poisoning" refers to poisoning caused by a neurotoxin. A neurotoxin is any chemical or substance that can cause neural death and thus neurological damage. An example of a neurotoxin is alcohol, which, when abused by a pregnant female, can result in alcohol poisoning and neurological damage known as Fetal Alcohol Syndrome in a newborn. Other examples of neurotoxins include, but are not limited to, kainic acid, domoic acid, and acromelic acid; certain pesticides, such as DDT; certain insecticides, such as organophosphates; volatile organic solvents such as hexacarbons (e.g. toluene); heavy a metals (e.g. lead, mercury, arsenic, and phosphorous); aluminum; certain chemicals used as weapons, such as Agent Orange and Nerve Gas; and neurotoxic antineoplastic agents.

"Neurodegeneration of the visual pathway" refers to neural cell death occurring in neurons involved in vision, for example neurons in the occipital lobe, optic nerve, and retina. Neurodegeneration of the visual pathway can be caused, for example, by a stroke in the visual pathway, for example a retinal stroke. Stoke can also occur in the optic nerve or the occipital lobe. Neurodegeneration of the visual pathway can also be caused by neurodegenerative diseases, for example macular degeneration. Neurodegeneration of the visual pathway can also be caused by diseases that are not necessarily considered neurodegenerative, such as glaucoma, which can cause retinal degeneration.

"Non-vascular headache" generally refers to headaches other than migraines. Examples of non-vascular headaches include, but are not limited to, stress headaches and sinus headaches.

The phrase "neurological damage" refers herein to neuron cell death.

The terms "treatment", "treating", and the like, refer to reversing, alleviating, or inhibiting the progress of the disease or condition to which such term applies, or one or more symptoms of such disease or condition. As used herein, these terms also encompass, depending on the condition of the patient, preventing the onset of a disease or condition, or of symptoms associated with a disease or condition. Such prevention also includes reducing the severity of a disease or condition or symptoms associated therewith prior to affliction with said disease or condition. Thus, "treatment" encompasses administration of the antagonist to a subject that is not at the time of administration afflicted with the disease or condition, and "treatment" can include preventing the recurrence of a disease or condition or of symptoms associated therewith. Conditions wherein a patient who is not at the time of examination afflicted with a disease or condition but could benefit from treatment according to a method described herein can be recognized by a healthcare professional, such as a medical doctor, of ordinary skill.

NR2B subunit selective NMDA antagonists that can be used in the methods of the present invention include compounds of formula I

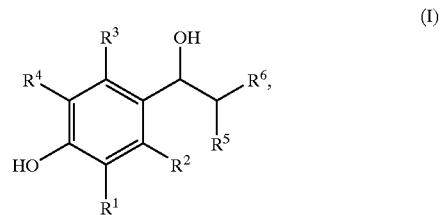

(I)

and pharmaceutically acceptable acid addition salt thereof, wherein:

(a) $R^2$ and $R^5$ are taken separately and $R^1$, $R^2$, $R^3$ and $R^4$ are each independently hydrogen, ($C_1$–$C_6$) alkyl, halo, $CF_3$, OH or $OR^7$ and $R^5$ is methyl or ethyl; or (b) $R^2$ and $R^5$ are, taken together,

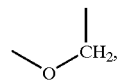

thereby forming a chroman-4-ol ring, and $R^1$, $R^3$ and $R^4$ are each independently hydrogen, ($C_1$–$C_6$) alkyl, halo, $CF_3$, OH or $OR^7$;

$R^6$ is

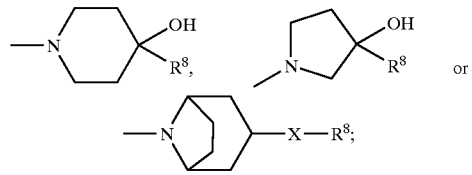

$R^7$ is methyl, ethyl, isopropyl or n-propyl;

$R^8$ is phenyl optionally substituted with up to three substituents independently selected from the group consisting of ($C_1$–$C_6$) alkyl, halo and $CF_3$;

X is O, S or $(CH_2)_n$; and n is 0, 1, 2, or 3.

Specific compounds of formula I that can be used are:

(+)-(1S,2S)-1-(4-hydroxy-phenyl)-2-(4-hydroxy-4-phenylpiperidino)-1-propanol;

(1S,2S)-1-(4-hydroxy-3-methoxyphenyl)-2-(4-hydroxy-4-phenylpiperidino)-1-propanol;

(3R,4S)-3-(4-(4-fluorophenyl)-4-hydroxypiperidin-1-yl)-chroman-4,7-diol;

pharmaceutically-acceptable salts of the above compounds; and (1R*,2R*)-1-(4-hydroxy-3-methylphenyl)-2-(4-(4-fluorophenyl)-4-hydroxypiperidin-1-yl)propan-1-ol;

and enantiomers of any of the aforementioned compounds;

and pharmaceutically acceptable acid addition salts of any of the aforementioned compounds and of any of their enantiomers.

The compounds of formula I can be prepared as follows. The compounds of formula I wherein $R^2$ and $R^5$ are taken together forming a chroman-4-ol ring, and $R^1$, $R^3$, and $R^4$ are hydrogen, can be prepared by one or more of the synthetic methods described and referred to in U.S. Pat. No. 5,356,905 (incorporated herein by reference, supra). The compounds of formula I wherein $R^2$ and $R^5$ are taken separately, and $R^1$, $R^2$, $R^3$ and $R^4$ are hydrogen can be prepared by one or more of the synthetic methods described and referred to in U.S. Pat. Nos. 5,185,343; 5,272,160; and 5,338,754; all of which are incorporated herein by reference in their entireties. The compounds of formula I can also be prepared by one or more of the synthetic methods described and referred to in U.S. patent application Ser. No. 08/292,651; U.S. Pat. No. 5,744,483 (issued Apr. 28, 1998) and U.S. Pat. No. 6,008,233 (issued Dec. 28, 1999); PCT International Application No. PCT/IB95/00398 which designates the United States (filed May 26, 1995) (corresponding to WO 96/37222); and PCT International Application No. PCT/IB95/00380 which designates the United States (filed May 18, 1995) (corresponding to WO 96/06081). These U.S. patents and PCT International Applications, and the U.S. patent application, are also all incorporated by reference herein in their entireties.

A preferred compound, (1S,2S)-1-(4-hydroxyphenyl)-2-(4-hydroxy-4-phenylpiperidin-1-yl)-1-proponal ((1S,2S) free base), and its tartrate salt, can be prepared as described in U.S. Pat. No. 5,272,160, referred to above. The resolution of racemic 1-(4-hydroxyphenyl)-2-(4-hydroxy-4-phenylpiperidin-1-yl)-1-propanol to form the (1S,2S) free base and the corresponding (1R,2R) enantiomer can be carried out as described in U.S. Pat. No. 6,008,233 (issued Dec. 28, 1999), referred to above, and as exemplified in Example 1 below.

The anhydrous mesylate of the (1S,2S) free base can be prepared as described in U.S. Pat. No. 5,272,160, referred to above. The anhydrous mesylate of the (1S,2S) free base, when equilibrated in an 81% relative humidity environment, will convert to the mesylate salt trihydrate of the (1S,2S) enantiomer.

The mesylate salt trihydrate of (1S,2S)-1-(4-hydroxyphenyl)-2-(4-hydroxy-4-phenylpiperidin-1-yl)-1-propanol can be prepared from the (1S,2S) free base as described in the U.S. Pat. No. 6,008,233, entitled "(1S,2S)-1-(4-Hydroxyphenyl)-2-(4-Hydroxy-4-Phenylpiperidin-1-yl)-1-Propanol Methanesulfonate Trihydrate", referred to above and incorporated herein by reference in its entirety. In this method, (1S,2S) free base is dissolved in water at 30° C. To this solution is added at least 1 equivalent of methane sulfonic acid and the resulting mixture is warmed to 60–65° C. The warm solution can be filtered to render it particulate free. The solution is concentrated to approximately 40% of the initial volume, cooled below 10° C., isolated by filtration and dried to a water content (measured Karl Fischer titration) of approximately 11.3%. The resulting crystalline mesylate salt trihydrate can be further purified by recrystallization.

Another preferred compound, (3R,4S)-3-[4-(4-fluorophenyl)-4-hydroxy-piperidin-1-yl]-chroman-4,7-diol ((3R,4S) chromanol), can be prepared as described in U.S. Pat. No. 5,356,905, U.S. Pat. No. 5,744,483 (issued Apr. 28, 1998), and U.S. provisional patent application entitled "Process For The Resolution Of Cis-Racemic 7-Benzyloxy-3-[4-(4-Fluorophenyl)-4-Hydroxy-Piperidin-1-yl]-Chroman-4-ol Dibenzoyl-D-Tartrate", all three of which are referred to above. The starting materials and reagents required for the synthesis of the (3R,4S) chromanol are readily available, either commercially, according to synthetic methods disclosed in the literature, or by synthetic methods exemplified in the description provided below.

The (3R,4S) chromanol can be prepared by fractional crystallization of the L-proline ester of racemic cis-7-benzyloxy-3-[4-(4-fluorophenyl)-4-hydroxy-piperidin-1-yl]-chroman-4-ol, as described in U.S. Pat. No. 5,744,483, referred to above. In a preferred method, the resolution method described in United States provisional patent application entitled "Process For The Resolution Of Cis-Racemic 7-Benzyloxy-3-[4-(4-Fluorophenyl)-4-Hydroxy-Piperidin-1-yl]-Chroman-4-ol Dibenzoyl-D-Tartrate", referred to above, and as exemplified in Example 3. In this method, the parent chromanol is prepared by dissolving racemic cis-7-benzyloxy-3-[4-(4-fluorophenyl)-4-hydroxy-piperidin-1-yl]-chroman -4-ol with an equal molar amount of dibenzoyl-D-tartaric acid in boiling aqueous ethanol. Racemic cis-7-benzyloxy-3-[4-(4-fluorophenyl)-4-hydroxy-piperidin-1-yl]-chroman-4-ol is prepared as described in U.S. patent application Ser. No. 08/189,479, referred to above. The concentration of aqueous ethanol is not critical and may be varied between 75% and 95% ethanol (ETOH). A concentration of 9:1/ETOH:$H_2O$ has been found to be effective and is preferred. A sufficient amount of the aqueous ethanol solvent to dissolve the racemic compound is required. This amount has been found to be about 17 ml per gram of racemic compound.

Upon stirring while heating under reflux, the racemic compound dissolves to form a hazy solution which is allowed to cool with stirring whereupon the (+) isomer, (3R,4S)-7-benzyloxy-3-[4-(4-fluorophenyl)-4-hydroxy-piperidin-yl]-chroman-4-ol dibenzoyl-D-tartrate, precipitates and may be collected by filtration and washed with aqueous ethanol. This is the tartrate salt of the (3R,4S) chromanol. The lactate and mandelate salts of the (3R,4S) chromanol are prepared in an analogous manner. This initial product is of about 90% optical purity. If a higher purity is desired, the product may be heated again with aqueous ethanol, cooled and the product collected and washed. Two such treatments were found to yield the (+) isomer of 99.4% optical purity in an overall yield of 74%. This method avoids a reduction step with lithium aluminum hydride and is therefore preferable for bulk operations. This method also can produce a significantly higher yield of the desired product.

The above described (+) isomer can be converted to (3R,4S)-3-[4-(4-fluorophenyl)-4-hydroxy-piperidin-1-yl]-chroman-4,7-diol by standard procedures. For example, treatment with dilute base can be used to free the piperidinyl base and subsequent hydrogenation removes the 7-benzyl group to yield the (3R,4S) chromanol.

NR2B subunit selective NMDA receptor antagonists useful in the practice of the invention may also be used in the form of a pharmaceutically acceptable salt. The expression "pharmaceutically-acceptable acid addition salts" is intended to include but not be limited to such salts as the hydrochloride, hydrobromide, sulfate, hydrogen sulfate, phosphate, hydrogen phosphate, dihydrogenphosphate, acetate, succinate, citrate, tartrate, lactate, mandelate, methanesulfonate (mesylate) and p-toluenesulfonate (tosylate) salts. The acid addition salts of the compounds of the present invention are readily prepared by reacting the base forms with the appropriate acid. When the salt is of a monobasic acid (e.g., the hydrochloride, the hydrobromide, the p-toluenesulfonate, the acetate), the hydrogen form of a dibasic acid (e.g., the hydrogen sulfate, the succinate) or the dihydrogen form of a tribasic acid (e.g., the dihydrogen phosphate, the citrate), at least one molar equivalent and usually a molar excess of the acid is employed. However when such salts as the sulfate, the hemisuccinate, the hydrogen phosphate or the phosphate are desired, the appropriate and exact chemical equivalents of acid will generally be used. The free base and the acid are usually combined in a co-solvent from which the desired salt precipitates, or can be otherwise isolated by concentration and/or addition of a non-solvent.

Any other compound that is an NR2B subunit selective NMDA receptor antagonist, including its pharmaceutically acceptable salts, can be used in the methods of this invention. NMDA receptor antagonists having NR2B subunit selectivity that may be used according to the present invention are, for example, described in U.S. Pat. Nos. 6,046,213; 5,185,343; 5,272,160; 5,338,754; and 5,356,905 (which issued, respectively, on Apr. 4, 2000; Feb. 9, 1993; Dec. 21, 1993; Aug. 16, 1994; and Oct. 18, 1994); U.S. Pat. No. 6,046,213 (issued Apr. 4, 2000), U.S. Pat. No. 5,744,483 (issued Apr. 28, 1998) and U.S. Pat. No. 6,008,233 (issued Dec. 28, 1999); PCT International Application No. PCT/IB95/00398 (filed May 26, 1995, corresponding to WO 96/37222); and PCT International Application No. PCT/IB95/00380 (filed May 18, 1995, corresponding to WO 96/06081). Other NR2B subunit selective NMDA receptor antagonists that may be used according to the present invention are described in WO 97/32581 (International Publication Date Sep. 12, 1997), WO 98/18793 (International Publication Date May 7, 1998), WO 97/23202 (International Publication Date Jul. 3, 1997), EP 0 824 098 A1 (Date of Publication, Feb. 18, 1998), EP 0846 683 A1 (Date of Publication, Jun. 10, 1998), and DE 19739331 (published Nov. 26, 1998). All of the foregoing patents and published patent applications are incorporated by reference herein in their entireties.

Other compounds that are indicated to bind selectively to NR2B NMDA receptor subunits that may be used according to the present invention are ifenprodil, supra, eliprodil (described in U.S. Pat. No. 4,690,931 (issued Sep. 1, 1987); and compounds described in WO 97/23458 (International Publication Date Jul. 3, 1997), WO 97/23216 (International Publication Date Jul. 3, 1997); WO 97/23215 (International Publication Date Jul. 3, 1997); and WO 97/23214 (International Publication Date Jul. 3, 1997). The preceding U.S. patent and PCT International Applications are incorporated by reference herein in their entireties.

Compounds that selectively antagonize NMDA receptors comprising an NR2B subunit by specifically binding to the NR2B subunit can be determined by screening compounds for inhibition of NMDA-induced current in recombinant *Xenopus* Oocytes cotransfected with the NR1A subunit and the NR2B subunit (see, e.g., Monyer, et al., *Science*, 1992, 256:1217–1221). A compound's activity in inhibiting current in the recombinant cells comprising the NR2B subunit can be compared to its activity inhibiting NMDA-induced current in recombinant *Xenopus* Oocytes expressing the NR1 subunit and NR2A, NR2C, and NR2D subunits. (See, Chenard and Menniti, supra).

One general method that can also generally predict whether or not a compound has NR2B subunit selectivity, for purposes of the present invention, is a standard competitive binding assay using [$^3$H] radiolabeled racemic CP-101,606 (which contains [$^3$H] (+)-(1S,2S)-1-(4-hydroxy-phenyl)-2-(4-hydroxy-4-phenylpiperidino)-1-propanol; see, for example, U.S. Pat. No. 6,046,213). If a compound has an $IC_{50}$ of less than about 5 $\mu$M for inhibition of racemic [$^3$H] CP-101,606 binding to the NR2B subunit, than the compound has NR2B subunit selectivity for purposes of the present invention. An example of such an assay is as follows:

Example of NR2B subunit binding assay. Selectivity of compounds for the NR2B-subunit containing NMDA receptor can be defined as an affinity for the racemic [$^3$H] CP-101,606 binding site in forebrain of rats, as described in Chenard and Menniti, supra. This affinity is assessed in a radioligand binding assay as described below. Selective compounds are preferably those which displace specific binding of racemic [$^3$H]CP-101,606 from rat forebrain membranes with an $IC_{50}$ of about $\leq 5$ $\mu$M.

The binding of racemic [$^3$H] (+)-(1S,2S)-1-(4-hydroxy-phenyl)-2-(4-hydroxy-4-phenylpiperidino)-1-propanol to rat forebrain membranes is measured as described by Menniti et al. (CP-101,606, a potent neuroprotectant selective for forebrain neurons, *European Journal of Pharmacology*, 1997, 331:117–126). Forebrains of adult male CD rats are homogenized in 0.32M sucrose at 4° C. The crude nuclear pellet is removed by centrifugation at 1,000×g for 10 min., and the supernatant centrifuged at 17,000×g for 25 min. The resulting pellet is resuspended in 5 mM Tris acetate pH 7.4 at 4° C. for 10 min. to lyse cellular particles and again centrifuged at 17,000×g. The resulting pellet is washed twice in Tris acetate, resuspended at 10 mg protein/ml and stored at −20° C. until use.

For binding assays, membranes are thawed, homogenized, and diluted to 0.5 mg protein/ml with 50 mM Tris HCl, pH 7.4. Compounds under study are added at various concentrations followed by racemic [$^3$H] CP-101,606 (specific activity 42.8 Ci/mmol, 5 nM final concentration). Following incubation for 20 min at 30° C. in a shaking water bath, samples are filtered onto Whatman GFB glass fiber filters using a MB-48R Cell Harvester (Brandel Research and Development Laboratories, Gaithersburg Md.). Filters are washed for 10 s with ice cold Tris HCl buffer and the radioactivity trapped on the filter quantified by liquid scintillation spectroscopy. Nonspecific binding is determined in parallel incubations containing 100 $\mu$M racemic CP-101,606. Specific binding is defined as total binding minus nonspecific binding.

In one embodiment of the present invention, an NR2B subunit selective NMDA antagonist is furthermore selective for NR2B subunit-containing NMDA receptors over $\alpha_1$-adrengergic receptors. For example, although ifenprodil (supra) has selectivity for the NR2B subtype of NMDA receptor, this compound is also a well known $\alpha_1$-adrenergic receptor antagonist. (Carter et al. *J. Pharmacol. Exp. Ther.*, 235, 475–482 (1990)). Compounds that antagonize $\alpha_1$-adrengergic receptors can cause a reduction in blood pressure that can be a complication to therapeutic use. Preferably, the NMDA antagonist has a ratio of NR2B receptor activity to $\alpha_1$-adrenergic receptor activity of at least about 3:1, more preferably at least about 5:1.

Affinity for the NR2B subunit containing NMDA receptor is measured as the $IC_{50}$ for displacement of specific binding of racemic [$^3$H] (+)-(1S,2S)-1-(4-hydroxy-phenyl)-2-(4-hydroxy-4-phenylpiperidino)-1-propanol from rat forebrain membranes (described above). Affinity for the $\alpha_1$-adrengergic receptor is defined as the $IC_{50}$ for displacement of specific binding of racemic [$^3$H]prazosin from rat brain membranes, measured as described by Greengrass and Bremner (*Binding Characteristics of [$^3$H]prazosin to Rat Brain $\alpha$-Adrenergic Receptors, European Journal of Pharmacology*, 55, 323–326, (1979)). A compound with a ratio of ([$^3$H]prazosin/[$^3$H] (+)-(1S,2S)-1-(4-hydroxy-phenyl)-2-(4-hydroxy-4-phenylpiperidino)-1-propanol) affinity greater than three is considered selective.

Forebrains of adult male Sprague Dawley rats are homogenized in 20 volumes of ice cold 50 mM Tris/HCl buffer (pH 7.7). The homogenate is centrifuged at 50,000×g for 10 min. at 4° C. The pellet is resuspended and centrifuged under identical conditions and the final pellet is resuspended in 80 volumes of 50 mM Tris/HCl (pH 8.0) at 4° C.

For binding assays, compounds under study are added at various concentrations to 500 µg membrane protein in 1 ml of 50 mM Tris/HCl buffer, followed by [$^3$H]prazosin (Amersham, specific activity 33 Ci/mmol, 0.2 nM final concentration). Following incubation for 30 min at 25° C. in a shaking water bath, samples are filtered onto Whatman GFB glass fiber filters using a MB-48R Cell Harvester (Brandel Research and Development Laboratories, Gaithersburg Md). Filters are washed three times for 10 s with ice cold Tris HCl buffer and the radioactivity trapped on the filter quantified by liquid scintillation spectroscopy. Nonspecific binding is determined in parallel incubations containing 100 nM prazosin. Specific binding is defined as total binding minus nonspecific binding.

An effective amount of the NR2B subunit selective NMDA antagonist for use on the present invention is typically from about 0.02 to 250 mg/kg/day (0.001–12.5 g/day in a typical human weighing 50 kg) in single or divided doses, regardless of route of administration. A more preferred dosage range is from about 0.15 mg/kg/day to about 250 mg/kg/day.

Of course, depending on the specific circumstances (for example, the presence or absence of a predisposition to the disease or condition being treated, the severity or expected severity of the disease, or the age or general health of the patient), even doses outside the aforementioned ranges may be in order. The particular dose given the specific circumstances can be determined by a physician or other healthcare professional of ordinary skill.

The NR2B subunit selective NMDA receptor antagonist useful in the method of the present invention is generally administered in the form of a pharmaceutical composition comprising one or more NR2B subunit selective NMDA receptor antagonists together with a pharmaceutically acceptable carrier or diluent.

The compositions described herein useful in the present invention are generally formulated in a conventional manner utilizing solid or liquid vehicles or diluents as appropriate to the mode of administration. For purposes of oral administration, tablets containing excipients such as sodium citrate, calcium carbonate and dicalcium phosphate may be employed along with various disintegrants such as starch and preferably potato or tapioca starch, alginic acid and certain complex silicates, together with binding agents such as polyvinylpyrrolidone, sucrose, gelatin and acacia. Additionally, lubricating agents such as, but not limited to, magnesium stearate, sodium lauryl sulfate and talc are often very useful for tableting purposes. Solid compositions of a similar type may also be employed as fillers in soft elastic and hard-filled gelatin capsules; preferred materials in this connection also include, by way of example and not of limitation, lactose or milk sugar as well as high molecular weight polyethylene glycols. When aqueous suspensions and/or elixirs are desired for oral administration, the essential active ingredient may be combined with various sweetening or flavoring agents, coloring matter or dyes and, if so desired, emulsifying and/or suspending agents, together with diluents such as water, ethanol, propylene glycol, glycerin and various like combinations thereof.

The present invention is illustrated by the following examples, but is not limited to the details thereof.

All nonaqueous reactions were run under nitrogen for convenience and generally to maximize yields. All solvents/diluents were dried according to standard published procedures or purchased in a predried form. All reactions were stirred either magnetically or mechanically. NMR spectra are recorded at 300 MHz and are reported in ppm. The NMR solvent was $CDCl_3$ unless otherwise specified. IR spectra are reported in $cm^{-1}$, generally specifying only strong signals.

EXAMPLE 1

Enantiomeric (1S,2S)- and (1R,2R)-1-(4-Hydroxyphenyl)-2-(4-hydroxy-4-phenylpiperidin-1-yl)-1-propanol (+)-Tartaric acid (300 mg, 2 mmol) was dissolved in 30 mL warm methanol. Racemic 1S*,2S*-1-(4-hydroxyphenyl)-2-(4-hydroxy-4-phenylpiperidin-1-yl)-1-propanol (655 mg, 2 mmol) was added all at once. With stirring and gentle warming a colorless homogeneous solution was obtained. Upon standing at ambient temperature 24 hours, 319 mg (66%) of a fluffy white precipitate was obtained. This product was recrystallized from methanol to give 263 mg of the (+)-tartrate salt of levorotatory title product as a white solid; mp 206.5–207.5° C.; $[alpha]_D$=−36.2°. This salt (115 mg) was added to 50 mL of saturated $NaHCO_3$. Ethyl acetate (5 mL) was added and the mixture was vigorously stirred 30 minutes. The aqueous phase was repeatedly extracted with ethyl acetate. The organic layers were combined and washed with brine, dried over calcium sulfate, and concentrated. The tan residue was recrystallized from ethyl acetate-hexane to give 32 mg (39%) of white, levorotatory title product; mp 203–204° C.; [alpha]$_D$=−58.4°. Anal. Calc'd. for $C_{20}H_{25}NO_3$: C, 73.37; H, 7.70; N, 4.28. Found: C, 72.61; H, 7.45; N, 4.21.

The filtrate from the (+)-tartrate salt preparation above was treated with 100 mL saturated aqueous $NaHCO_3$ and extracted well with ethyl acetate. The combined organic extracts were washed with brine, dried over calcium sulfate and concentrated to give 380 mg of recovered starting material (partially resolved). This material was treated with (−)-tartaric acid (174 mg) in 30 mL of methanol as above. After standing for 24 hours, filtration gave 320 mg (66%) of product which was further recrystallized from methanol to produce 239 mg of the (−)-tartrate salt of dextrorotatory title product; mp 206.5–207.5° C. [alpha]$_D$=+33.9°. The latter was converted to dextrorotatory title product in the manner above in 49% yield; mp 204–205° C.; [alpha]$_D$=+56.9°. Anal. Found: C, 72.94; H, 7.64; N, 4.24.

EXAMPLE 2

(1S,2S)-1-(4-hydroxyphenyl)-2-(4-hydroxy-4-phenylpiperidin-yl)-1-propanol methanesulfonate trihydrate Step 1

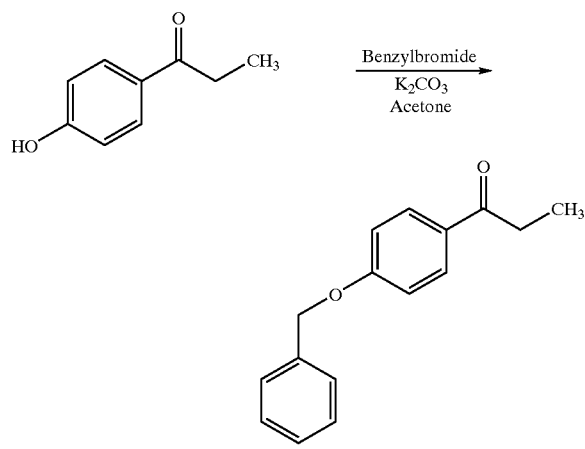

A 50 gallon glass lined reactor was charged with 17.1 gallons of acetone, 8.65 kilograms (kg) (57.7 mol) of 4'-hydroxypropiophenone, 9.95 kg (72.0 mol) of potassium carbonate and 6.8 liters (l) (57.7 mol) of benzylbromide. The mixture was heated to reflux (56° C.) for 20 hours. Analysis of thin layer chromatography (TLC) revealed that the reaction was essentially complete. The suspension was atmospherically concentrated to a volume of 10 gallons and 17.1 gallons of water were charged. The suspension was granulated at 25° C. for 1 hour. The product was filtered on a 30" Lapp and washed with 4.6 gallons of water followed by a mixture of 6.9 gallons of hexane and 2.3 gallons of isopropanol. After vacuum drying at 45° C., this yielded 13.35 kg (96.4%) of the above-depicted product.

A second run was carried out with 9.8 kg (65.25 mol) of 4'-hydroxypropiophenone using the procedure described above. After drying 15.1 kg (96.3%) of the above-depicted product was obtained.

Step 2

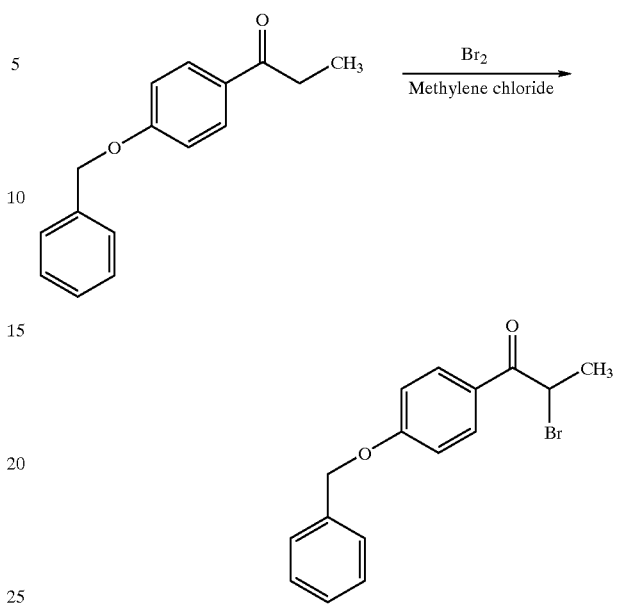

Under a nitrogen atmosphere, a 100 gallon glass lined reactor was charged with 75 gallons of methylene chloride and 28.2 kg (117.5 mol) of the product from step 1. The solution was stirred five minutes and then 18.8 kg of bromine was charged. The reaction was stirred for 0.5 hours at 22° C. Analysis of TLC revealed that the reaction was essentially complete. To the solution was charged 37 gallons of water and the mixture was stirred for 15 minutes. The methylene chloride was separated and washed with 18.5 gallons of saturated aqueous sodium bicarbonate. The methylene chloride was separated, atmospherically concentrated to a volume of 40 gallons and 60 gallons of isopropanol was charged. The concentration was continued until a pot temperature of 80° C. and final volume of 40 gallons were obtained. The suspension was cooled to 20° C. and granulated for 18 hours. The product was filtered on a 30" Lapp and washed with 10 gallons of isopropanol. After vacuum drying at 45° C., this yielded 29.1 kg (77.6%) of the above-depicted product.

Step 3

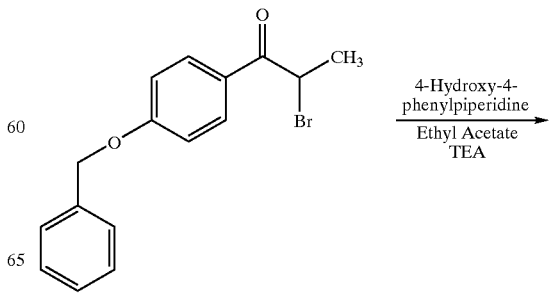

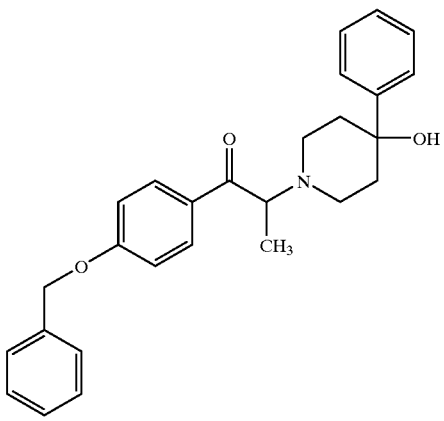

Under a nitrogen atmosphere, a 20 gallon glass lined reactor was charged with 4.90 kg (15.3 mol) of the product from step 2, 7.0 gallons of ethyl acetate, 2.70 kg (15.3 mol) of 4-hydroxy-4-phenylpiperidine and 1.54 kg of triethylamine (15.3 mol). The solution was heated to reflux (77° C.) for 18 hours. The resulting suspension was cooled to 20° C. Analysis by TLC revealed that the reaction was essentially complete. The byproduct (triethylamine hydrobromide salt) was filtered on a 30" Lapp and washed with 4 gallons of ethyl acetate. The filtrate was concentrated under vacuum to a volume of 17 liters. The concentrate was charged to 48 liters of hexane and the resulting suspension granulated for 2 hours at 20° C. The product was filtered on a 30" Lapp and washed with 4 gallons of hexane. After vacuum drying at 50° C., this yielded 4.9 kg (77%) of the above-depicted product.

A second run was carried out with 3.6 kg (11.3 mol) of the product from step 2 using the procedure described above. After drying 4.1 kg (87%) of the above-depicted product was obtained.

Step 4

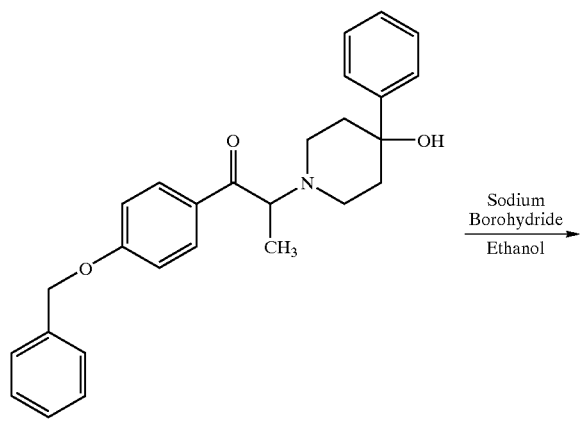

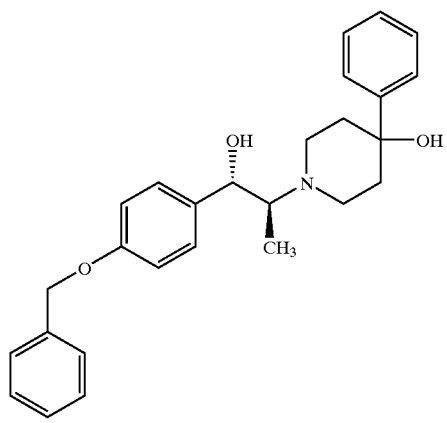

"Threo isomer"

Under a nitrogen atmosphere, a 100 gallon glass lined reactor was charged with 87.0 gallons of 2B ethanol and 1.7 kg (45.2 mol) of sodium borohydride. The resulting solution was stirred at 25° C. and 9.4 kg (22.6 mol) of the product from step 3 was charged. The suspension was stirred for 18 hours at 25–30° C. Analysis by TLC revealed that the reaction was essentially complete to the desired threo diastereoisomer. To the suspension was charged 7.8 liters of water. The suspension was concentrated under vacuum to a volume of 40 gallons. After granulating for 1 hour, the product was filtered on a 30" Lapp and washed with 2 gallons of 2B ethanol. The wet product, 9.4 gallons of 2B-ethanol and 8.7 gallons of water were charged to a 100 gallon glass lined reactor. The suspension was stirred at reflux (78° C.) for 16 hours. The suspension was cooled to 25° C., filtered on 30" Lapp and washed with 7 gallons of water followed by 4 gallons of 2B ethanol. After air drying at 50° C., this yielded 8.2 kg (86.5%) of the above-depicted product. This material was recrystallized in the following manner.

A 100 gallon glass lined reactor was charged with 7.9 kg (18.9 mol) of the product from step 3, 20 gallons of 2B ethanol and 4 gallons of acetone. The suspension was heated to 70° C. producing a solution. The solution was concentrated atmospherically to a volume of 15 gallons. The suspension was cooled to 25° C. and granulated for 1 hour. The product was filtered on a 30" Lapp. The wet product and 11.7 gallons of 2B ethanol was charged to a 100 gallon glass lined reactor. The suspension was heated to reflux (78° C.) for 18 hours. The suspension was cooled to 25° C., filtered on a 30" Lapp and washed with 2 gallons of 2B ethanol. After air drying at 50° C. this yielded 5.6 kg (70.6%) of the above-depicted product.

Step 5

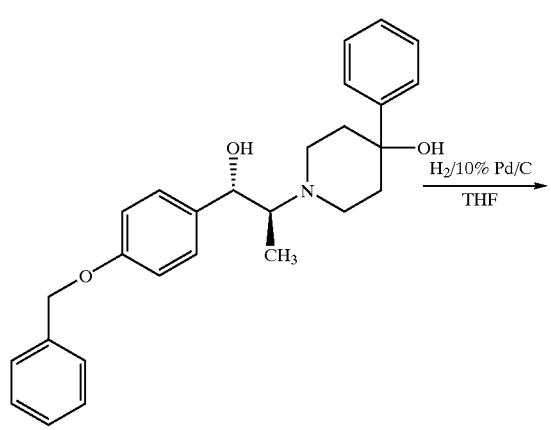

"Threo isomer"

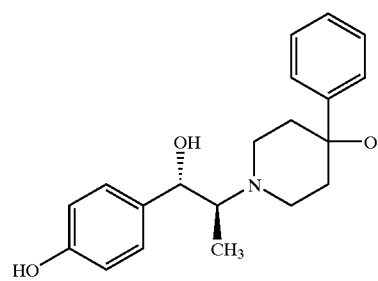

Under a nitrogen atmosphere, a 50 gallon glass lined reactor was charged with 825 g of 10% palladium on carbon (50% water wet), 5.5 kg (13.2 mol) of the product from step 4 and 15.5 gallons of tetrahydrofuran (THF). The mixture was hydrogenated between 40–50° C. for 2 hours. At this time, analysis by TLC revealed that the reduction was essentially complete. The reaction was filtered through a 14" sparkler precoated with Celite and washed with 8 gallons of THF. The filtrate was transferred to a clean 100 gallon glass lined reactor, vacuum concentrated to a volume of 7 gallons and 21 gallons of ethyl acetate were charged. The suspension was atmospherically concentrated to a volume of 10 gallons and a pot temperature of 72° C. The suspension was cooled to 10° C., filtered on a 30" Lapp and washed with 2 gallons of ethyl acetate. After air drying at 55° C. this yielded a 3.9 kg (90%) of the above-depicted product (i.e., the free base).

Step 6

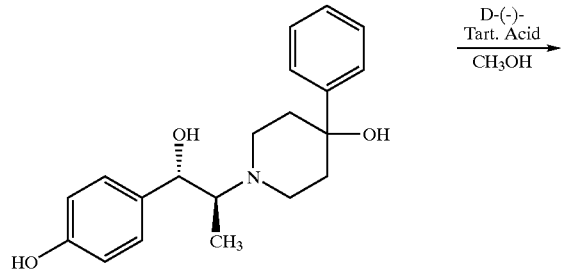

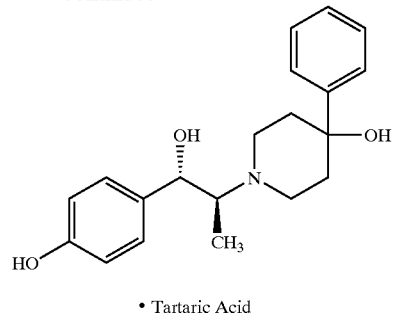

• Tartaric Acid

A 100 gallon glass lined reactor was charged with 20 gallons of methanol and 3.7 kg (11.4 mol) of the product from step 5 (i.e., the free base). The suspension was heated to 60° C. and 1.7 kg (11.4 mol) of D-(−)-tartaric acid were charged. The resulting solution was heated to reflux (65° C.) for 3 hours after which a suspension formed. The suspension was cooled to 35° C., filtered on a 30" Lapp and washed with 1 gallon of methanol. The wet solids were charged to a 100 gallon glass lined reactor with 10 gallons of methanol. The suspension was stirred for 18 hours at 25° C. The suspension was filtered on a 30" Lapp and washed with 2 gallons of methanol. After air drying at 50° C. this yielded 2.7 kg (101%) of the above-depicted product (i.e., the tartaric acid salt of the free base (R-(+)-enantiomer)). This material was purified in the following manner:

A 100 gallon glass lined reactor was charged with 10.6 gallons of methanol and 2.67 kg (5.6 mol) of the above tartaric acid salt. The suspension was heated to reflux (80° C.) for 18 hours. The suspension was cooled to 30° C., filtered on a 30" Lapp and washed with 4 gallons of methanol. After air drying at 50° C., this yielded 2.05 kg (76.7%) of the above-depicted product (i.e., the tartaric acid salt of the free base).

Step 7

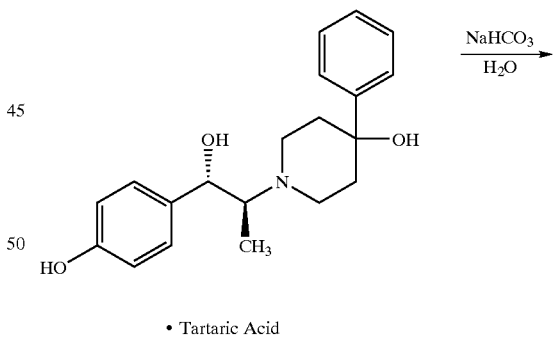

• Tartaric Acid

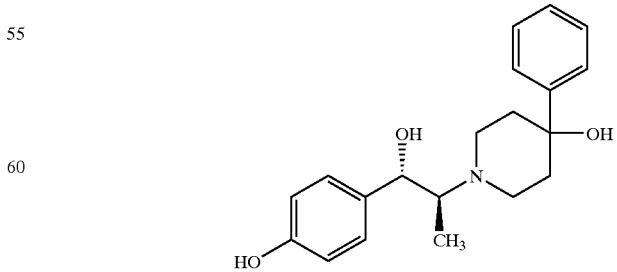

A 55 liter nalgene tub was charged with 30 liters of water and 1056 g (12.6 mol) of sodium bicarbonate at 20° C. To the resulting solution was charged 2.0 kg (4.2 mol) of the product from step 6 (i.e., the tartaric acid salt of the free base). The suspension was stirred for 4 hours during which a great deal foaming occurred. After the foaming ceased, the suspension was filtered on a 32 cm funnel and washed with 1 gallon of water. After air drying at 50° C., this yielded 1.28 kg (93.5%) of the above-depicted product (i.e., the free base).

Step 8

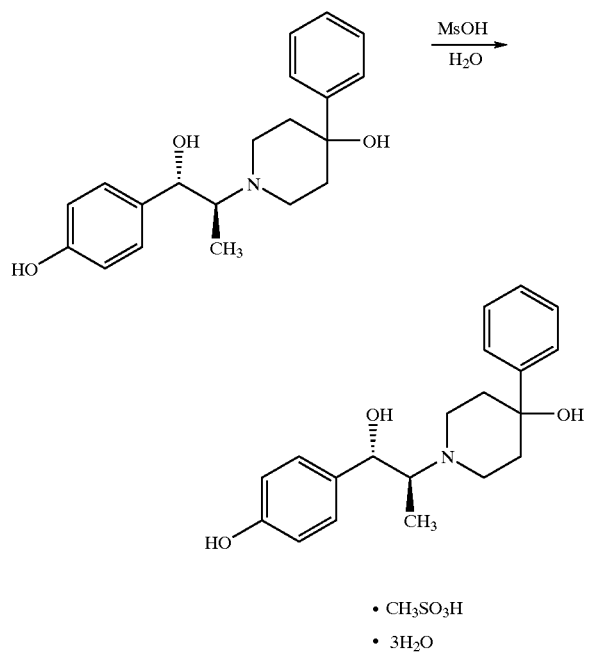

A 22 liter flask was charged with 1277 g (3.9 mol) of product from step 7 and 14 liters of water. The suspension was warmed to 30° C. and 375 g (3.9 mol) of methane sulfonic acid were charged. The resulting solution was warmed to 60° C., clarified by filtering through diatomaceous earth (Celite™) and washed with 2 liters of water. The speck-free filtrate was concentrated under vacuum to a volume of 6 liters. The suspension was cooled to 0–5° C. and granulated for 1 hour. The product was filtered on an 18" filter funnel and washed with 635 ml of speck-free water. After air drying at 25° C. for 18 hours, this yielded 1646 g (88%) of the above-depicted product (i.e., the mesylate salt trihydrate).

EXAMPLE 3

(1R*,2R*)-1-(4-hydroxy-3-methylphenyl)-2-(4-(4-fluorophenyl)-4-hydroxypiperidin-1-yl)-propan-1-ol-mesylate A mixture of 3-methyl-4-triisopropylsilyloxy-α-bromopropiophenone (9.17 g, 22.97 mmol), 4-(4-fluorophenyl)-4-hydroxypiperidine (6.73g, 34.45 mmol) and triethylamine (8.0 mL, 57.43 mmol) in ethanol (180 mL) was refluxed for 6 hours. The solvent was removed at reduced pressure and the residue was partitioned between ethyl acetate and water. The phases were separated and the organic layer was washed with brine, dried over calcium sulfate and concentrated. The residue was flash chromatographed on silica gel (3×3.5 inches packed in hexane) with elution proceeding as follows: 10% ethyl acetate/hexane (1000 mL), nil; 20% ethyl acetate/hexane (700 mL), nil; 20% ethyl acetate/hexane (1300 mL) and 25% ethyl acetate/hexane (600 mL), 7.66 g (65%) of 1-(3-methyl-4-triisopropylsilyloxyphenyl)-2-(4-(4-fluorophenyl)-4-hydroxypiperidin-1-yl)-propan-1-one as a yellow foam which was suitable for use without further purification. A sample recrystallization from ethyl acetate/hexane as white crystals had: m.p. 78–82° C.

A mixture of sodium borohydride (0.564 g, 14.92 mmol) and ethanol (60 mL) was stirred 10 minutes and then 1-(3-methyl-4-triisopropylsilyloxyphenyl)-2-(4-(4-fluorophenyl)-4-hydroxypiperidin-1-yl)-propan-1-one (7.66 g, 14.92 mmol in 10 mL of ethanol) was added with two 30 mL ethanol rinses. The reaction mixture was stirred at ambient temperature overnight. The white solid that precipitated was collected by filtration and dried to yield 5.72 g (74%) of (1R*,2R*)-1-(3-methyl-4-triisopropylsilyloxyphenyl)-2-(4-(4-fluorophenyl)-4-hydroxypiperidin-1-yl)-1-ol, which was suitable for use without further purification and had: m.p. 188–189° C.

The product of the above reaction (5.72 g, 11.1 mmol) was dissolved in tetrahydrofuran (150 mL) and tetrabutylammonium fluoride (12.21 mL, 12.21 mmol, 1M tetrahydrofuran solution) was added. The reaction was stirred 1 hour at ambient temperature and then concentrated. The residue was partitioned between ethyl acetate and water and the two phases were separated. The organic layer was slurried with methylene chloride. The white solid that precipitated was collected by filtration and dried to afford 3.41 g (85%) of (1R*,2R*)-1-(4-hydroxy-3-methylphenyl)-2-(4-(4-fluorophenyl)-4-hydroxypipeidin-1-yl)-propan-1-ol. A sample (0.16 g, 0.447 mmol) was converted to the corresponding mesylate salt. The salt was slurried in methanol (8 mL) and methanesulfonic acid (0.029 mL, 0.45 mmol) was added. The mixture was filtered and concentrated. The mixture was then recrystallized from ethanol to give 0.152 g (58%) of the mesylate salt which had: m.p. 215–216° C. Analysis calculated for $C_{21}H_{25}FNO_3 \cdot CH_4SO_3$: C, 58.01; H, 6.64, N, 3.07. Found: C, 57.99; H, 6.72; N, 3.17.

EXAMPLE 4

1R,2R1-(4-hydroxy-3-methoxyphenyl)-2-(4-hydroxy-4-phenyl-piperidin-1-yl)-propan-1-ol and 1S,2S 1-(4-hydroxy-3-methoxyphenyl)-2-(4-hydroxy-4-phenyl-piperidin-1-yl)-propan-1-ol A mixture of 2-bromo-1-(2,2-diphenyl-benzo(1,3)dioxol-5-yl)-propan-1-one (2.00 g, 4.89 mmol), 4-hydroxy-4-phenylpiperidine (0.9 g, 5.08 mmol) and triethylamine (1.40 mL, 10.04 mmol) in ethanol (50 mL) was refluxed overnight. The solvent was removed at reduced pressure and the residue was partitioned between ether and water. The phases were separated and the organic layer was washed with brine, dried over magnesium sulfate and concentrated. The residue was flash chromatographed on silica gel (2×5 inches packed with hexane) with elution proceeding as follows: 20% ethyl acetate/hexane (500 mL), unweighed forerun; 50% ethyl acetate/hexane (500 mL), 1.76 g (71%) of 1-(2,2)-diphenyl-benzo(1,3)dioxol-5-yl)-2-(4-hydroxy-4-phenylpiperidin-1- yl)-propan-1-one as light tan foam which was suitable for use without further purification and had: NMR δ 7.81 (dd, J=1.7, 8.3 Hz, 1H), 7.70 (d, J=1.6Hz, 1H), 7.64–7.13 (m, 15H), 6.92 (d, J=8.2 Hz, 1H), 4.07 (q, J=7.0 Hz, 1H), 3.39–3.27 (m, 1H), 2.94–2.59 (m, #H), 2.30–2.04 (m, 2H), 1.74 (br t, J=13.2 Hz, 2H), 1.30 (d, J=6.8 Hz, 3H).

A mixture of sodium borohydride (0.15 g, 3.97 mmol) and ethanol (5 mL) was stirred 10 minutes and then 1-(2,2-diphenyl-benzo(1,3)dioxol-5-yl)-2-(4-hydroxy-4-phenylpiperidin-1-yl)propan-1-one (1.70 g, 3.36 mmol in 20 mL of ethanol) was added. The reaction was stirred at ambient temperature over the weekend. The white precipitate was collected, rinsed with ethanol and ether and air dried to afford 1.35 g of crude product. The product was recrystallized from ethanol/ethyl acetate/methylene chloride to give 1.05 g (61%) of 1R*,2R*)-1-(2,2-diphenyl-benzo(1,3)dioxol-5-yl)-2-(4-hydroxy-4-phenylpiperidin-1-yl) propan-1-ol which had: mp 224–224.5° C. Analysis calculated for $C_{33}H_{33}NO_4$: C, 78.08; H, 6.55; N, 2.76. Found: C, 78.16; H, 6.46; N, 2.72.

A mixture of the product of the above reaction (1.00 g, 1.97 mmol) and 10% palladium on carbon (0.175 g) in methanol (50 mL) and acetic acid (1.0 mL) was hydrogenated at 50 psi (initial pressure) for 5 hours at ambient temperature. Additional catalyst (0.18 g) was added and the hydrogenation was continued overnight. The reaction was filtered through diatomaceous earth and the filter pad was rinsed with methanol. The filtrate was concentrated and the residue was partitioned between ethyl acetate and saturated aqueous bicarbonate and stirred vigorously for 1 hour. The phases were separated and the aqueous layer was extracted with ethyl acetate (2×). The combined organic layer was washed with water and brine, dried over magnesium sulfate and concentrated. The residue was flash chromatographed on silica gel (1×4 inches) with elution proceeding as follows: 20% ethyl acetate/hexane (500 mL), nil; 10% methanol/ethyl acetate (250 mL), 20% methanol/ethyl acetate (250 mL), and 50% methanol/ethyl acetate, 0.51 g (75%) of a light yellow-green solid. The solid was recrystallized from ethanol to afford (1R*,2R*)-1-(3,4-dihydroxyphenyl)-2-(4-hydroxy-4-phenyl-piperidin-1-yl)-propan-1-ol as a white solid which had: mp 167–168° C. Analysis calculated for $C_{20}H_{25}NO_4 \cdot 0.5\ C_2H_6O$: C, 68.83; H, 7.70; N, 3.82. Found: C, 68.78; H, 8.05; N, 3.70.

The racemic product was dissolved in ethanol and separated into enantiomers by HPLC using the following chromatographic conditions: Column, Chiralcel OD; mobile phase, 25% ethanol/75% hexane; temperature, ambient (approximately 22° C.); detection, UV at 215 nM. Under these conditions, 1R,2R1-(4-hydroxy-3-methoxyphenyl)-2-(4-hydroxy-4-phenyl-piperidin-1-yl) propan-1-ol eluted with a retention time of approximately 9.12 minutes and 1S,2S 1-(4-hydroxy-3-methoxyphenyl)-2-(4-hydroxy-4-phenyl-piperidin-1-yl)propan-1-ol eluted with a retention time of approximately 16.26 minutes.

EXAMPLE 5

(3R*,4S)-3-(4-(4-fluorophenyl)-4-hydroxypiperidin-1-yl)-chroman-4,7-diol

A mixture of 7-benzyloxy-3,3-dibromochromanone (54.7 g, 133 mmol), 4-(4-fluorophenyl)-4-hydroxypiperidine (52.0 g, 266 mmol), and triethylamine (38 mL, 270 mmol) in acetonitrile (2.5 L) was stirred 16 hours at ambient temperature. A yellow precipitate formed and was collected, washed well with water and ether, and air dried. The yield of 7-benzyloxy-3-{4-(4-fluorophenyl)-4-hydroxy-pipridine-1-yl]-chromenone was 55.4 g (93%) which was suitable for use without further purification. A sample recrystallized from ethanol/tetrahydrofuran had mp 220–221° C.: NMR $DMSO_{do}$ δ7.99 (d, J=9 Hz, 2H), 7.56–7.40 (m, 8H), 7.18–7.08 (m, 4H), 5.25 (s, 2H), 5.06 (s, 1H), 3.60 (br s, 1 H), 3.55–3.35 (m, 1 H, partially obscured by water from the NMR solvent), 3.10–2.95 (m, 2H), 2.15–2.00 (m, 2H), 1.71 (br t, J=13.7 Hz, 2H).

Analysis calculated for $C_{27}H_{24}FNO_4$: C, 72.80; H, 5.43; N, 3.13. Found: C, 72.83; H, 5.82; N, 2.82.

To a slurry of 7-benzyloxy-3-[4-(4-fluorophenyl)-4-hydroxy-piperidine-1-yl]-chromenone (8.24 g, 18.5 mmol) in ethanol (400 mL) and tetrahydrofuran (600 mL) was added sodium borohydride (7.0 g, 185 mmol). The mixture was stirred overnight. Additional sodium borohydride (7.0 g) was added and the reaction mixture was stirred for 3 days. Water was added and the solvent was removed at reduced pressure at 45° C. The solids which formed were collected and washed well with water and then ether. The solid was further dried in vacuo overnight to give 5.01 g, 60% of 3R*4S*7-benzyloxy-3-[4-(4-fluorophenyl)-4-hydroxy-piperidin-1-yl]-chroman-4l-ol which was suitable for use without further purification. A sample recrystallized from ethyl acetate/chloroform had mp. 194–195° C.; NMR δ7.56–7.30 (m, 8H), 7.06 (long range coupled t, J=8.7 Hz, 2H) 6.63 (dd, J=2.4, 8.5 Hz, 1H), 6.47 (d, J=2.4 Hz, 1H), 5.04 (s, 2H), 4.77 (d, J=4.5 Hz, 1H), 4.37 (dd, J=3.5, 10.4 Hz, 1H), 4.13 (t, J=10.4 Hz, 1H), 3,82 (brs, 1H), 3.11 (br d, J=11.2 Hz, 1H), 2.92–2.71 (m, 4H), 2.21–2.06(m, 2H), 1.87–1.73 (m, 2H), 1.54 (s, 1 H).

Analysis calculated for $C_{27}H_{28}FNO_4$: C, 72.14; H, 6.28; N, 3.12. Found C, 72.15; H, 6.21; N, 3.12.

A mixture of 3R*4S*7-benzyloxy-3-[4-(4-fluorophenyl)-4-hydroxy-piperidin-1-yl]-chroman-4-ol (0.80 g, 1.78 mmol), 10% palladium on carbon (0.16 g), methanol (40 mL), and acetic acid (0.8 mL) was hydrogenated for 8 hours with a starting pressure of 48.5 psi. The reaction was filtered through celite and the filtrate was concentrated. The residue was stirred vigorously with ether and saturated sodium bicarbonate for 1 hour. The solid was washed with water and ether and dried in vacuo. Recrystallization from ethanol yielded 0.35 g (54%) of 3R*4S*3-[4-(4-fluorophenyl)-4-hydroxy-piperidin-1-yl]-chroman-4,7-diol as a white solid which had mp 159–160° C.; NMR $DMSO_{do}$ δ7.55–7.47 (m, 2H), 7.11 (t, J=9 Hz, 2H), 7.02 (d, J=8.4 Hz, 1H)k, 6.32 (dd, J=2.3, 8.3 Hz, 1H), 6.15 (d, J=2.3 Hz 1H), 5.10–4.50 (br m with s at 4.63, 3H), 4.23 (dd, J=2.8, 10.3 Hz, 1H), 4.04 (t, J=10.5 Hz, 1H), 2.99 (br d, J=10.8 Hz, 1H), 2.86 (br d, J=10.7 Hz, 1H), 2.73–2.50 (m, 3H), 2.08–1.90 (m, 2H), 1.58 (br d, J=13 Hz, 2H).

Analysis calculated for $C_{20}H_{22}FNO_4 \cdot 0.25H_2O$; C, 66.01; H, 6.23; N, 3.85. Found: C, 66.22; H, 6.58; N. 3.46.

What is claimed is:

1. A method of treating depression in a mammal, which method comprises administering to the mammal an amount of an NR2B subunit selective NMDA antagonist, which amount is effective in treating depression, wherein the NR2B subunit selective NMDA receptor antagonist is a compound of the formula

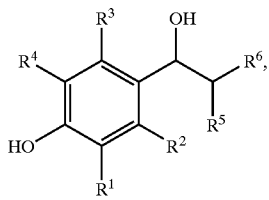

(I)

or a pharmaceutically acceptable acid addition salt thereof, wherein:

(a) $R^2$ and $R^5$ are taken separately and $R^1$, $R^2$, $R^3$ and $R^4$ are each independently hydrogen, $(C_1-C_6)$ alkyl, halo, $CF_3$, OH or $OR^7$ and $R^5$ is methyl or ethyl; or (b) $R^2$ and $R^5$ are taken together and are

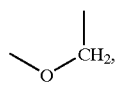

forming a chroman-4-ol ring, and $R^1$, $R^3$ and $R^4$ are each independently hydrogen, $(C_1-C_6)$ alkyl, halo, $CF_3$, OH or $OR^7$;

$R^6$ is

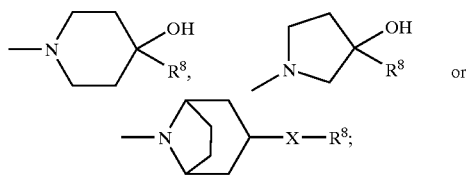

$R^7$ is methyl, ethyl, isopropyl or n-propyl;

$R^8$ is phenyl optionally substituted with up to three substituents independently selected from the group consisting of $(C_1-C_6)$ alkyl, halo and $CF_3$;

X is O, S or $(CH_2)_n$; and n is 0, 1, 2, or 3.

2. A method according to claim 1, wherein the NR2B subunit selective NMDA receptor antagonist is (+)-(1S,2S)-1-(4-hydroxy-phenyl)-2-(4-hydroxy-4-phenylpiperidino)-1-propanol;

(1S,2S)-1-(4-hydroxy-3-methoxyphenyl)-2-(4-hydroxy-4-phenylpiperidino)-1-propanol;

(3R,4S)-3-(4-(4-fluorophenyl)-4-hydroxypipendin-1-yl)-chroman-4,7-diol;

a pharmaceutically-acceptable acid addition salt of one of said compounds; or (1R*,2R*)-1-(4-hydroxy-3-methylphenyl)-2-(4-(4-fluorophenyl)-4-hydroxypiperidin-1-yl)-propan-1-ol-mesylate.

* * * * *